(12) United States Patent
Guette et al.

(10) Patent No.: US 9,523,691 B2
(45) Date of Patent: Dec. 20, 2016

(54) USE OF THE OLFACTOMEDIN-4 PROTEIN (OLFM4) IN COLORECTAL CANCER DIAGNOSIS

(75) Inventors: Catherine Guette, La Possonniere (FR); Olivier Coqueret, Angers (FR); Benjamin Barre, Brain sur Longuenee (FR); Erick Gamelin, Paris (FR)

(73) Assignee: INSTITUT DE CANCEROLOGIE DE L'OUEST, Angers (FR)

( * ) Notice: Subject to any disclaimer, the term of this patent is extended or adjusted under 35 U.S.C. 154(b) by 0 days.

(21) Appl. No.: 14/002,225

(22) PCT Filed: Mar. 2, 2011

(86) PCT No.: PCT/IB2011/000787
§ 371 (c)(1),
(2), (4) Date: Jan. 27, 2014

(87) PCT Pub. No.: WO2012/117267
PCT Pub. Date: Sep. 7, 2012

(65) Prior Publication Data
US 2013/0336969 A1 Dec. 19, 2013

(51) Int. Cl.
| | | |
|---|---|---|
| G01N 33/53 | (2006.01) | |
| G01N 33/574 | (2006.01) | |
| A61K 31/4745 | (2006.01) | |
| A61K 31/513 | (2006.01) | |
| A61K 31/519 | (2006.01) | |
| A61K 33/24 | (2006.01) | |
| A61K 39/395 | (2006.01) | |
| A61K 45/06 | (2006.01) | |
| C12Q 1/68 | (2006.01) | |
| A61K 31/555 | (2006.01) | |
| G01N 1/28 | (2006.01) | |

(52) U.S. Cl.
CPC ..... *G01N 33/57488* (2013.01); *A61K 31/4745* (2013.01); *A61K 31/513* (2013.01); *A61K 31/519* (2013.01); *A61K 31/555* (2013.01); *A61K 33/24* (2013.01); *A61K 39/395* (2013.01); *A61K 39/39558* (2013.01); *A61K 45/06* (2013.01); *C12Q 1/6886* (2013.01); *G01N 33/57419* (2013.01); *C12Q 2600/118* (2013.01); *G01N 2001/284* (2013.01)

(58) Field of Classification Search
None
See application file for complete search history.

(56) References Cited

PUBLICATIONS

Koshida et al (Cancer Sci, 2007, 98(3): 315-320).*
Watanabe et al (Cancer, 2009, 115(2): 283-292).*
Tournigand et al (J Clin Oncol, 2004, 22(2): 229-237).*
Liu et al (Experimental Cell Research, 2006, 1785-1797).*
Alfonso et al., "Proteomic expression analysis of colorectal cancer by two-dimensional differential gel electrophoresis," Proteomis, 2005, vol. 5, pp. 2602-2611.
Allegra et al., "American Society of Clinical Oncology Provisional Clinical Opinion: Testing for KRAS Gene Mutations in Patients With Metastatic Colorectal Carcinoma to Predict Response to Anti-Epidermal Growth Factor Receptor Monoclonal Antibody Therapy," J Clin Oncology, Apr. 2009, vol. 27, No. 12, pp. 2091-2906.
Andreyev et al., "Kirsten ras mutations in patients with colorectal cancer: the 'RASCAL II' study," British J Cancer, 2001, vol. 85, No. 5, pp. 692-696.
Bi et al., "Proteomic Analysis of Colorectal Cancer Reveals Alterations in Metabolic Pathways," Mol Cell Proteomics 5.6, 2006, pp. 1119-1130.
Bos J.L., "Ras Oncogenes in Human Cancer: A Review," Cancer Res, Sep. 1989, vol. 49, pp. 4682-4689.
Casado et al., "Molecular markers in colorectal cancer: genetic bases for a customised treatment," Clin Transl Oncol, 2007, vol. 9, pp. 549-554.
Conrotto et al., "Identification of new accessible tumor antigens in human colon cancer by ex vivo protein biotinylation and comparative mass spectrometry analysis," Int. J. Cancer, 2008, vol. 123, pp. 2856-2864.
Del Rio et al., "Gene Expression Signature in Advanced Colorectal Cancer Patients Select Drugs and Response for the Use of Leucovorin, Fluorouracil, and Irinotecan," J Clin Oncology, Mar. 2007, vol. 25, No. 7, pp. 773-780.
Ernoult et al., "Improved proteome coverage by using iTRAQ labelling and peptide OFFGEL fractionation," Proteome Science, 2008, vol. 6, No. 27, 13 pages.
Etienne-Grimaldi et al., "K-Ras Mutations and Treatment Outcome in Colorectal Cancer Patients Receiving Exclusive Fluoropyrimidine Therapy," Clin Cancer Res, Aug. 2008, vol. 14, No. 15, pp. 4830-4835.
Grant et al., "Quantification of Protein Expression Changes in the Aging Left Ventricle of *Rattus norvegicus*," J Proteome Research, 2009, vol. 8, No. 9, pp. 4252-4263.
Jervoise et al., "Kirsten ras Mutations in Patients With Colorectal Cancer: the Multicenter 'RASCAL' Study," J Nat'l Cancer Institute, May 1998, vol. 90, No. 9, pp. 675-684.
Kabakchiev et al., "Gene Expression Changes Associated with Resistance to Intravenous Corticosteroid Therapy in Children with Severe Ulcerative Colitis," PLoS One, Sep. 2010, vol. 5, No. 9, e13085, pp. 1-8.

(Continued)

*Primary Examiner* — Sean Aeder
(74) *Attorney, Agent, or Firm* — Foley & Lardner LLP

(57) ABSTRACT

The present invention provides a method for diagnosing KRAS mutations in colorectal cancers by measuring the level of OLFM4. In another aspect, the present invention relates a method of predicting the responds to a chemotherapeutic agent of a subject suffering from a colorectal cancer: according to the present invention, the by determining the OLFM4 levels. According to the present invention, the response can be predicted by determining the OLFM4 levels. This result in turn permits the design or the adaptation of a treatment of the said subject with the said chemotherapeutic agent.

11 Claims, 5 Drawing Sheets

(56) References Cited

PUBLICATIONS

Figure 1:
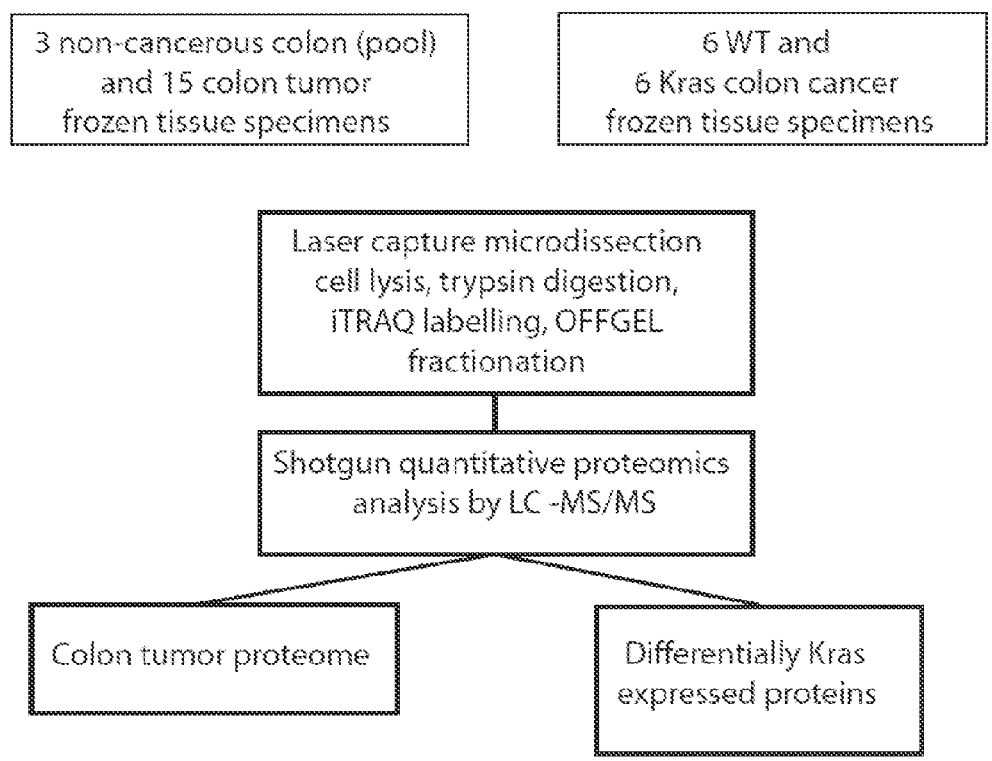

Kim et al., "Up regulation of GW112 Gene by NFκB Promotes an Antiapoptotic Property in Gastric Cancer Cells," Molecular Carcinogenesis, 2010, vol. 49, pp. 259-270.

Koshida et al., "Specific overexpression of OLFM4$^{GW112/hGC-1}$ mRNA in colon, breast and lung cancer tissues detected using quantitative analysis," Cancer Sci, Mar. 2007, vol. 98, No. 3, pp. 315-320.

Kranenburg O., The KRAS oncogene: Past, present, and future, Biochimica et Biophysica Acta, 2005, vol. 1756, pp. 81-82.

Lee et al., "Gene Expression Profiling of Metaplastic Lineages Identifies CDH17 as a Prognostic Marker in Early Stage Gastric Cancer," Gastroenterology, 2010, vol. 139, No. 1, pp. 213-225 (including 225.e1-225.e3).

Li et al., "Proteomics Identification of Cyclophilin A as a Potential Prognostic Factor and Therapeutic Target in Endometrial Carcinoma," Mol Cell Proteomics 7.10, 2008, pp. 1810-1823.

Liu et al., "Reduced hGC-1 Protein Expression Is Associated with Malignant Progression of Colon Carcinoma," Clin Cancer Res, 2008, Feb. 2008, vol. 14, No. 4, pp. 1041-1049.

Madoz-Gúrpides et al., "A Proteomics Analysis of Cell Signaling Alterations in Colorectal Cancer," Mol Cell Proteomics 6.12, 2007, pp. 2150-2164.

Mojica et al., "Normal colon epithelium: a dataset for the analysis of gene expression and alternative splicing events in colon disease," BMC Genomics, 2010, vol. 11, No. 5, 14 pages.

Oue et al., "Serum olfactomedin 4 (GW112, hGC-1) in combination with Reg IV is a highly sensitive biomarker for gastric cancer patients," Int. J. Cancer, 2009, vol. 125, pp. 2383-2392.

Poston et al., "Urgent Need for a New Staging System in Advanced Colorectal Cancer," J Clin Oncology, Oct. 2008, vol. 26, No. 29, pp. 4828-4833.

Roebler et al., "Identification of Nicotinamide N-Methyltransferase as a Novel Serum Tumor Marker for Colorectal Cancer," Clin Cancer Res, Sep. 2005, vol. 11, No. 18, pp. 6550-6557.

Roessler et al., "Identification of PSME3 as a Novel Serum Tumor Marker for Colorectal Cancer by Combining Two-dimensional Polyacrylamide Gel Electrophoresis with a Strictly Mass Spectrometry-based Approach for Data Analysis," Mol Cell Proteomics 5.11, 2006, pp. 2092-2101.

Schetter et al., "Association of Inflammation-Related and microRNA Gene Expression with Cancer-Specific Mortality of Colon Adenocarcinoma," Clin Cancer Res, Sep. 2009, vol. 15, No. 18, pp. 5878-5887.

Schwacke et al., "iQuantitator: A tool for protein expression inference using iTRAQ," BMC Bioinformatics, 2009, vol. 10, No. 342, 15 pages.

Smith et al., "Activating K-Ras mutations outwith 'hotspot' codons in sporadic colorectal tumours—implications for personalised cancer medicine," British J Cancer, 2010, vol. 102, No. 4, pp. 693-703.

Tomarev et al., "Olfactomedin Domain-Containing Proteins: Possible Mechanisms of Action and Functions in Normal Development and Pathology," Mol Neurobiol., Oct. 2009, vol. 40, No. 2, pp. 122-138.

Uemura et al., "Identification and Characterization of a Diamine Exporter in Colon Epithelial Cells," J. Biol. Chem., Sep. 2008, vol. 283, No. 39, pp. 26428-26435.

Van Der Flier et al., "OLFM4 Is a Robust Marker for Stem Cells in Human Intestine and Marks a Subset of Colorectal Cancer Cells," Mini-Reviews and Perspectives, 2009, pp. 15-17.

Wang et al., "Comparative Proteomics Approach to Screening of Potential Diagnostic and Therapeutic Targets for Oral Squamous Cell Carcinoma," Mol Cell Proteomics 7.9, 2008, pp. 1639-1650.

Watanabe et al., "Differential gene expression signatures between colorectal cancers with and without KRAS mutations: Crosstalk between the KRAS pathway and other signaling pathways," European J Cancer, 2011, vol. 47, pp. 1946-1954.

Zanivan et al., "Solid Tumor Proteome and Phosphoproteome Analysis by High Resolution Mass Spectrometry," J Proteome Research, 2008, vol. 7, No. 12, pp. 5314-5326.

Zhang et al., "GW112, A Novel Antiapoptotic Protein That Promotes Tumor Growth," Cancer Research, Apr. 2004, vol. 64, pp. 2474-2481.

Zhang et al., "Identification and characterization of a novel member of olfactomedin-related protein family, hGC-1, expressed during myeloid lineage development," Gene, 2002, vol. 283, pp. 83-93.

International Search Report issued in application No. PCT/IB2011/000787 on Nov. 25, 2011.

* cited by examiner

SEQUENCE LISTING

```
<160> NUMBER OF SEQ ID NOS: 14

<210> SEQ ID NO 1
<211> LENGTH: 22
<212> TYPE: DNA
<213> ORGANISM: artificial
<220> FEATURE:
<223> OTHER INFORMATION: Primer

<400> SEQUENCE: 1
aaccttatgt gtgacatgtt ct                                              22

<210> SEQ ID NO 2
<211> LENGTH: 21
<212> TYPE: DNA
<213> ORGANISM: artificial
<220> FEATURE:
<223> OTHER INFORMATION: Primer
<220> FEATURE:
<221> NAME/KEY: misc_feature
<222> LOCATION: (1)..(1)
<223> OTHER INFORMATION: Biotinylation

<400> SEQUENCE: 2
tcgtccacaa aatgattctg a                                               21

<210> SEQ ID NO 3
<211> LENGTH: 17
<212> TYPE: DNA
<213> ORGANISM: artificial
<220> FEATURE:
<223> OTHER INFORMATION: Primer

<400> SEQUENCE: 3
cttgtggtag ttggagc                                                    17

<210> SEQ ID NO 4
<211> LENGTH: 24
<212> TYPE: DNA
<213> ORGANISM: artificial
<220> FEATURE:
<223> OTHER INFORMATION: Primer

<400> SEQUENCE: 4
ttatggcaaa tacacaaaga aagc                                            24

<210> SEQ ID NO 5
<211> LENGTH: 23
<212> TYPE: DNA
<213> ORGANISM: artificial
<220> FEATURE:
<223> OTHER INFORMATION: Primer
<220> FEATURE:
<221> NAME/KEY: misc_feature
<222> LOCATION: (1)..(1)
<223> OTHER INFORMATION: Biotinylation

<400> SEQUENCE: 5
```

```
cagactgtgt ttctcccttc tca                                            23
```

<210> SEQ ID NO 6
<211> LENGTH: 18
<212> TYPE: DNA
<213> ORGANISM: artificial
<220> FEATURE:
<223> OTHER INFORMATION: Primer

<400> SEQUENCE: 6

```
atattctcga cacagcag                                                  18
```

<210> SEQ ID NO 7
<211> LENGTH: 18
<212> TYPE: DNA
<213> ORGANISM: artificial
<220> FEATURE:
<223> OTHER INFORMATION: Primer

<400> SEQUENCE: 7

```
gccatgactc agattcct                                                  18
```

<210> SEQ ID NO 8
<211> LENGTH: 18
<212> TYPE: DNA
<213> ORGANISM: artificial
<220> FEATURE:
<223> OTHER INFORMATION: Primer

<400> SEQUENCE: 8

```
cagggcttc ttatagtg                                                   18
```

<210> SEQ ID NO 9
<211> LENGTH: 20
<212> TYPE: DNA
<213> ORGANISM: artificial
<220> FEATURE:
<223> OTHER INFORMATION: Primer

<400> SEQUENCE: 9

```
tgtgcaggtg ggtgtagttg                                                20
```

<210> SEQ ID NO 10
<211> LENGTH: 20
<212> TYPE: DNA
<213> ORGANISM: artificial
<220> FEATURE:
<223> OTHER INFORMATION: Primer

<400> SEQUENCE: 10

```
ccaggcacaa ggctaagagt                                                20
```

<210> SEQ ID NO 11
<211> LENGTH: 22
<212> TYPE: DNA
<213> ORGANISM: artificial
<220> FEATURE:
<223> OTHER INFORMATION: Primer

<400> SEQUENCE: 11

```
ttcgccgaga aatcgtggct ct                                             22
```

<210> SEQ ID NO 12
<211> LENGTH: 23
<212> TYPE: DNA

```
<213> ORGANISM: artificial
<220> FEATURE:
<223> OTHER INFORMATION: Primer

<400> SEQUENCE: 12
agctgaacca cagacggttt gct                                           23

<210> SEQ ID NO 13
<211> LENGTH: 20
<212> TYPE: DNA
<213> ORGANISM: artificial
<220> FEATURE:
<223> OTHER INFORMATION: Primer

<400> SEQUENCE: 13
aacccagctc tggagaaact                                               20

<210> SEQ ID NO 14
<211> LENGTH: 20
<212> TYPE: DNA
<213> ORGANISM: artificial
<220> FEATURE:
<223> OTHER INFORMATION: Primer

<400> SEQUENCE: 14
cccctggaga ttttagtggt                                               20
```

USE OF THE OLFACTOMEDIN-4 PROTEIN (OLFM4) IN COLORECTAL CANCER DIAGNOSIS

With 655,000 deaths worldwide per year, colorectal cancer is the third most common form of cancer and the second leading cause of cancer-related death in the Western world. Management of colorectal cancer patients and selection of the best treatment protocol is thus a crucial health problem. The selection of the appropriate treatment is crucial for the patient, as well as for health economics reasons.

The main options for colorectal cancer therapy are surgery and or chemotherapy, depending on the individual patient's tumor staging and other age and cobormibidity factors.

Two types of situations are encountered by the oncologist:
1. In case of localized primary tumor, the main question is the indication of adjuvant chemotherapy after surgery. It is essential to select poor prognosis tumors requiring heavy and aggressive initial chemotherapy protocol in order to prevent secondary metastases. Otherwise, the survival of the patient might be highly compromised. For example, in case of invaded proximal lymph nodes, the risk of secondary metastases is 70% at 5 years. On the other hand, adding an aggressive adjuvant chemotherapy to surgery when not needed can lead to adverse toxic side-effects that may significantly affect the patient's quality of life or even his own life. In addition, since the median age of patients with colorectal cancer is 69, these patients, who are often with comorbidities, are at higher risk of severe toxic side-effects.
   Furthermore, innovative targeted therapies are very expensive (around 5,000 Euros per month) and should be used only when needed and with high chances of efficacy.
2. 50% of the patients with colorectal cancer will have secondary metastases that can be treated only with chemotherapy agents and targeted therapies. Efficacy of these drugs is often impaired by tumor cells resistance mechanisms, such as transduction signal protein or transcription factor overexpression or mutation, resulting in tumor proliferation or survival. There is thus a great need for new tests permitting to assess the resistance factors of a particular colorectal tumor, in order to be able to select the adapted treatment.

In conclusion, there is still a need for the identification and characterization of reliable tumor prognosis markers or resistance predictive factors in order to facilitate the identification of tumors, that 1) really need adjuvant chemotherapy or 2) require an optimized chemotherapy protocol.

Tumor resistance to treatment most often implies transduction signal or antiapoptotic proteins overexpression or mutation.

One of the most important proteins involved in MAP kinase transduction signal is KRAS. KRAS is a member of the rat sarcoma virus (ras) gene family of oncogenes (including KRAS, HRAS, and NRAS) and encodes the guanosine diphosphate (GDP)- and guanosine triphosphate (GTP)-binding protein RAS that acts as a major intracellular signal transducer. After binding and activation by GTP, RAS recruits the oncogene RAF, which phosphorylates MAP2K-1 (mitogen-activated protein kinase kinase-1) and MAP2K-2, thus initiating MAPK (mitogen-activated protein kinase) signaling that ultimately leads to expression of proteins playing important roles in cell growth, differentiation, and survival. Mutation in KRAS, BRAF, or PIK3CA results in continuous activation of the downstream RAS-MAPK or PI3K pathways. Such activation in turn enhances transcription of various oncogenes involved in abnormal cell cycle progression, including MYC, AP1, CREB, and NF-κB (7,8,9).

KRAS is one of the commonly mutated oncogenes in human cancers. In particular, KRAS mutations are found in 30-40% of tumors and represent together with APC one of the somatic alteration involved in the initiation of colorectal cancer. This mutation occurs early in the process of carcinogenesis, and is maintained at the various stages of disease progression, such as node involvement and metastatic spread. A recent study involving a large number of patients has demonstrated that mutated KRAS is associated with worse outcome in colorectal cancer progression, with effects being more pronounced in stage II and III disease (Nash, et al., *Ann. Surg. Oncol.,* 17: 416-424, 2010). The same group has shown, in another study (Nash, et al., *Ann. Surg. Oncol.,* 17: 572-578, 2010), that KRAS mutation is associated with more rapid and aggressive metastatic behavior of colorectal liver metastases.

In addition, KRAS mutation has been reported to induce drug resistance and treatment failure to epidermal-growth factor receptor (EGFR)-targeting therapeutics in metastatic colorectal cancer. KRAS mutations confer resistance to both cetuximab (Erbitux®) and panitumumab (Vectibix®) (Allegra et al., *J. Clin. Oncol.,* 27: 2091-2096, 2008; Linardou et al., *Lancet Oncol.,* 9: 962-972, 2008). Consequently, KRAS genotyping is required in metastatic colorectal cancer before selecting a targeted therapy and wild type Kras gene is mandatory before anti EGFR drugs administration.

Kras is actually a cornerstone for tumor resistance. Not only are KRAS mutations responsible for resistance to both cetuximab and panitumumab, they have been recently shown to confer colorectal tumor resistance to a platinum derivative agent, oxaliplatin (Richman et al., *J Clin Oncol,* 27(35): 5866-5867, 2009). Moreover, if adding anti EGFR-targeting drug to irinotecan has no effect, either positive or negative, in the treatment of KRAS mutated tumors, adding the said drug to oxaliplatin leads to deleterious effects (Douillard et al., *J Clin Oncol,* 28(31): 4697-4705 2010).

Commercial KRAS tests based on the identification of specific KRAS mutations are commercially available. However, a comparability study revealed a lack of agreement between the said KRAS testing assays (Oliner et al., *Diagn Pathol.,* 5: 23, 2010). Moreover, these tests may not accurately identify heterogeneous tumors, i.e. tumors wherein some cells only carry KRAS mutations. Thus there is still a need for other test for determining the presence of KRAS mutations in colorectal cancers.

The present inventors have now shown that overexpression of olfactomedin 4 (OLFM4) is associated with a higher risk of carrying a KRAS mutation. Moreover, olfactomedin 4 overexpression is linked to chemotherapy treatment resistance.

OLFM4 is a member of olfactomedin domain-containing protein family that has a relatively diverse coil-coil domain in the amino terminus and a well-conserved olfactomedin domain in the carboxy-terminus. The olfactomedin 4 protein is a secreted N-glycosylated protein, which can be assayed in the blood of patients. The OLFM4 gene is highly expressed in myeloid differentiation in active inflammatory bowel disease, and in certain cancers suggesting that OLFM4 might play an important role in cellular differentiation, inflammation, and cancer evolution (Zheng et al, *Blood,* 103: 1883-1890, 2004; Liu et al, *Exp Cell Res.,* 312(10): 1785-1797, 2006). A series of studies have reported that OLFM4 is involved in regulating cellular apoptosis and the proliferation of cancer cells (Zhang et al, *Cancer Res.*, 64: 2474-2481, 2004; Kobayashi et al, *Cancer Sci.*, 98(3): 334-340, 2007). In particular, OLFM4 is overexpressed in colon cancer (Koshida et al., *Cancer Sci.*, 98(3): 315-320, 2007) and the concentration of circulating olfactomedin 4 is higher in the blood of colorectal cancer patients than in the blood of control healthy people (Yasui et al., *Int J Cancer.*, 125(10): 2383-2392, 2009). However, another study disclosed that reduced olfactomedin 4 protein expression is associated with malignant progression of colon carcinoma (Liu et al., *Clin. Cancer Res.*, 14(4): 1041-1049, 2008). On the other hand, none of these studies suggested a relation between overexpression of olfactomedin 4 and the presence of a KRAS mutation. Moreover, none of these studies suggested a relation between overexpression of olfactomedin 4 and the presence of a KRAS mutation in metastatic colorectal tumors. By "metastatic colorectal tumor", it is herein referred to a stage III or stage IV colorectal cancer.

In a first aspect, the present invention thus provides a method for diagnosing the presence of a KRAS mutation in a patient's colorectal cancer. According to the method of the invention, elevated expression levels of the OLFM4 gene and/or olfactomedin 4 protein indicate the presence of the said KRAS mutation. Preferably, the colorectal cancer is a metastatic colorectal tumor.

Therefore, the invention relates to a method for determining the presence of a KRAS mutation in a metastatic colorectal cancer, said method comprising the steps of:

(a) determining from a biological sample of a metastatic colorectal tumor-suffering subject the expression level of OLFM4,
(b) comparing the obtained expression level with at least one reference expression level, and
(c) determining the presence of a KRAS mutation in the said metastatic colorectal tumor from said comparison.

By "olfactomedin 4", it is herein referred to a secreted, N-glycosylated protein of 510 residues, said protein comprising an olfactomedin domain. Preferentially, the said protein is a human protein. Even more preferentially, the said protein has an amino acid sequence as in NP_006409.3, and the OLFM4 gene, which encodes the said protein, has a nucleotide sequence as in NM_006418.3. The OLFM4 gene is conserved in chimpanzee, dog, cow, mouse, rat, chicken, and zebrafish; should the need arise, the person skilled in the art would easily be able to identify the corresponding gene in any of these species on the basis of the sequence homology of the said gene with the above-mentioned human gene.

The present inventors have shown that the presence of a KRAS mutation in a colorectal cancer leads to overexpression of the OLFM4 gene in turn results in the overexpression of the olfactomedin 4 protein. It is thus possible to determine OLFM4 gene expression levels either by measuring the amount of the OLFM4 nucleic acid transcript (i.e. based on the OLFM4 mRNA content of the sample) or of the olfactomedin 4 protein (i.e. based on the olfactomedin 4 protein content of the sample).

The KRAS-mutated colorectal tumors preferentially express the glycosylated form of the said olfactomedin 4. Therefore, the expression level of OLFM4 can also be determined by measuring the glycosylated olfactomedin 4 protein levels, i.e. by measuring the amount of the glycosylated form of the olfactomedin 4 protein. Advantageously, the amount of the glycosylated form is compared to the level of the non glycosylated form, with a ratio of glycosylated versus non glycosylated forms of the olfactomedin 4 protein higher than 1.4 indicating the presence of KRAS mutation in the colorectal cancer; preferentially, the said ratio is higher than 1.5; more preferentially, it is higher than 1.6; even more preferentially, it is higher than 1.7. In this particular embodiment, the method of the invention comprises the additional steps of measuring the amount of the glycosylated form of the olfactomedin 4 protein, measuring the amount of the non glycosylated form of the olfactomedin 4 protein, and calculating the ratio of glycosylated versus non glycosylated forms of the olfactomedin 4 protein.

In addition to being glycosylated, the said olfactomedin 4 protein is preferentially secreted, as evidenced by the preferential localization in secretion vesicles of the said olfactomedin 4 protein in KRAS-mutated tumor cells, as compared to non-mutated tumor cells or healthy tissue. It is thus also possible to detect the expression level of OLFM4 by measuring the amount of olfactomedin 4 protein. This can be achieved either by measuring directly the amount of secreted protein from a biological sample which does not contain any tumor cell, or, in an indirect way, by quantifying in the tumor cells the secretion vesicles which contain the said olfactomedin 4 protein.

In another aspect, OLFM4 levels can be used to determine if a patient will respond or not to chemotherapy treatment. The present inventors have shown that overexpression of OLFM4 confers resistance to chemotherapy treatment. For example, overexpression of OLFM4 increases the survival of colorectal cancer cells in the presence of genotoxic agents, such as oxaliplatin and sn38 (the active metabolite of irinotecan. More specifically, the presence of secreted olfactomedin 4 in the medium is sufficient to promote resistance of colon cancer cells to the said agents. It should also be mentioned that the efficacy of an EGFR-targeting agent for treating colorectal cancer is dependent upon the absence of any KRAS mutation. It has indeed been demonstrated that patients with mutated KRAS in their colorectal cancer do not respond to treatment with EGFR-targeting agents or oxaliplatin. High OLFM4 levels are thus indicative of a poor response, or an absence of response to chemotherapeutic agent treatment.

The invention thus relates to a method for the in vitro diagnosis or prognosis of a chemotherapeutic agent-responding or non-responding phenotype, comprising:

(a) determining from a biological sample of a colorectal cancer-suffering subject the expression level of OLFM4,
(b) comparing the obtained expression level with at least one reference expression level, and
(c) determining the chemotherapeutic agent responding or non-responding phenotype from said comparison.

"Chemotherapy" as used herein is a cancer treatment that uses drugs to stop the growth of cancer cells, either by killing the cells or by stopping them from dividing. The said drug can be for example a small molecule: small molecules which can be conveniently used for the invention include in particular genotoxic drugs. Preferably, genotoxic drugs used for colorectal cancer treatment include busulfan, bendamustine, carboplatin, carmustine, chlorambucil, cisplatin, cyclophosphamide, dacarbazine, daunorubicin, doxorubicin, epirubicin, etoposide, idarubicin, ifosfamide, irinotecan (and its active metabolite sn38), lomustine, mechlorethamine, melphalan, mitomycin c, mitoxantrone, oxaliplatin, temozolamide and topotecan. Even more preferentially, the genotoxic drugs according to the invention are oxaliplatin, irinotecan, and irinotecan active metabolite sn38. However, the invention should not be understood as being limited to genotoxic drugs, as many other types of small molecules can also be used in the context of this invention. For example, antimetabolites such as 5-FU (and its pro-drug capecitabine), tegafur-uracil (or UFT or UFUR), leucovorin (LV, folinic acid), or proteasome inhibitors such as bortezomib are also encompassed by the scope of this invention.

Chemotherapy can also be performed with biological drugs. A biological drug according to the invention is any type of biological agent which has a therapeutic activity in colorectal cancer therapy. The said agent can be for example an antisense oligonucleotide (e.g. oblimersen), but it is preferentially a protein such as a soluble VEGF receptor, e.g. aflibercept, or an antibody. In a further preferred embodiment, the said agent is a monoclonal antibody (e.g. bevacuzimab, i.e. Avastin®).

Another preferred group of chemotherapeutic drugs according to the invention corresponds to the EGFR-targeting agents. By "EGFR-targeting agent" or "ETA", it is herein meant an agent which is capable of neutralizing the effects of EGFR, i.e. an inhibitor of EGFR. By "Epidermal-Growth Factor" or "EGFR", it is herein referred to a cell-surface receptor for members of the epidermal growth factor family (EGF-family) of extracellular protein ligands. The EGFR protein according to the invention is a human polypeptide having an aminoacid sequence as laid out in NP_005219. Advantageously, the said agent of the invention is capable of inhibiting the downstream signalling of EGFR. Thus this class of agents is distinguished on the basis of its target, not by its nature (i.e. small molecule or biotherapeutic). Included within the definition of ETA are small molecules which bind to and inhibit EGFR, such as gefitinib, erlotinib, vandetanib, BIBW 2992, lapatinib, or neratinib. ETAs according to the invention also encompass antibodies, and in particular monoclonal antibodies. In a preferred embodiment, the said agent is selected in the group consisting of panitumumab (Vectibix®), mastuzumab, and cetuximab (Erbitux®). In an even more preferred embodiment, the said agent is cetuximab (Erbitux®).

The invention also relates to a method for designing treatment with a chemotherapeutic agent for a subject suffering from a colorectal cancer, said method comprising:
(a) determining from a biological sample of a colorectal cancer-suffering subject the expression level of OLFM4,
(b) comparing the obtained expression level with at least one reference expression level,
(c) determining chemotherapeutic agent-responding or non-responding phenotype from said comparison, and
(d) designing the dose of chemotherapeutic agent treatment according to said identified chemotherapeutic agent-responding or non-responding phenotype.

For the purposes of this application, it is understood that when the phenotype determined in step (a) is a non-responding phenotype, the dose of chemotherapeutic treatment determined in step (b) may be equal to 0.

Optionally, the dose of chemotherapeutic agent determined in step (b) is administered to the subject. If the dose is equal to 0, then no treatment is given.

The invention is also drawn to a method of treatment of a colorectal cancer-suffering subject with a chemotherapy agent, comprising:
(a) determining from a biological sample of the said colorectal cancer-suffering subject the presence of a chemotherapeutic agent-responding or non-responding phenotype using a method according to the invention, and
(b) adapting the chemotherapeutic agent treatment in function of the result of step (a).

Said adaptation of the chemotherapeutic agent treatment may consist in:

a reduction or suppression of the said chemotherapeutic agent treatment if the subject has been diagnosed as chemotherapeutic agent non-responding, or
the continuation of the said treatment with said chemotherapeutic agent if the subject has been diagnosed as chemotherapeutic agent-responding.

The invention also refers to a new use of a chemotherapeutic agent in the treatment of colorectal cancer, comprising the steps of:
(a) determining from a biological sample of the said colorectal cancer-suffering subject the presence of a chemotherapeutic agent-responding or non-responding phenotype using a method according to the invention, and
(b) determining the dose of chemotherapeutic agent to administer with respect to the result of step (a).

Optionally, the dose of chemotherapeutic agent determined in step (b) is administered to the subject. As mentioned above, if the dose is equal to 0, then no treatment is given.

The invention thus relates to a chemotherapeutic agent to treat colorectal cancer, wherein the chemotherapeutic agent is administered to a colorectal cancer-suffering subject who has been diagnosed and/or prognosed as responsive using a method according to the invention. More specifically, the invention relates to a chemotherapeutic agent to treat colorectal cancer in a subject suffering from a colorectal cancer, wherein:
(a) the chemotherapeutic agent-responding or non-responding phenotype of the said subject is determined according to the method of the invention,
(b) the dose of chemotherapeutic agent treatment according to said identified chemotherapeutic agent-responding or non-responding phenotype, and
(c) the dose of the chemotherapeutic agent which is determined in step (b) is administered to the said subject.

Commonly used first line chemotherapy regimens for colorectal cancer involve the combination of infusional 5-fluorouracil, leucovorin, and oxaliplatin (FOLFOX) with cetuximab or panitumumab, or of infusional 5-fluorouracil, leucovorin, and irinotecan (FOLFIRI) with cetuximab or panitumumab, both in KRAS wild type tumors.

The invention thus also refers to a method of treatment of a colorectal cancer-suffering subject, comprising the steps of:
(a) administering a therapeutic dose of FOLFOX or FOLFIRI to the said subject suffering from colorectal cancer,
(b) determining from a biological sample of the said colorectal cancer-suffering subject the presence of a chemotherapeutic agent-responding or non-responding phenotype using a method according to the invention, and
(c) determining the dose of chemotherapeutic agent to administer with respect to the result of step (b).

Thus the invention also refers to a combination of chemotherapeutic agent and FOLFOX or chemotherapeutic agent and FOLFIRI for the treatment of colorectal cancer, comprising the steps of:
(a) administering a therapeutic dose of FOLFOX or FOLFIRI to a subject suffering 5 from colorectal cancer,
(b) determining from a biological sample of the said colorectal cancer-suffering subject the presence of a chemotherapeutic agent-responding or non-responding phenotype using a method according to the invention, and
(c) determining the dose of chemotherapeutic agent to administer with respect to the 10 result of step (b).

Optionally, the dose of chemotherapeutic agent determined in step (c) is administered to the subject.

According to the present invention, a "chemotherapeutic agent responding phenotype" is defined as a response state of a subject to the administration of a chemotherapeutic agent. A "response state" means that the said subject (referred to as a chemotherapeutic agent responding subject or a responding subject or a responsive subject: for the purpose of this application, these terms are similar) responds to the treatment, i.e. that the treatment is efficacious in the said subject. The definition of response is a reduction of tumor volume as assessed by e.g. CT-Scan or Magnetic resonance imaging (MRI). These criteria are thus well known to the skilled person in the art and need not be detailed here.

In contrast, a "chemotherapeutic agent non-responding phenotype" refers to the absence in said subject (referred to herein as an chemotherapeutic agent non-responding subject or a non responding subject or a non-responsive subject: these terms should be construed in the context of this application as having the same meaning) of a state of response, meaning that said subject remains refractory to the treatment.

In a preferred embodiment of any of the above-described in vitro methods of diagnosis/prognosis according to the invention, the said subject is a colorectal cancer-suffering subject. A "colorectal cancer-suffering subject" is a subject with a cancer at any of the stages of the classification used by the person skilled in the art. In other words, any subject with a stage 0, a stage I, a stage IIA, a stage IIB, a stage IIIA, a stage IIIB, a stage IIIC, or a stage IV colorectal cancer, is a colorectal cancer-suffering subject as understood herein. In one further embodiment, the said subject is not treated with a chemotherapeutic agent; in another further embodiment, the said subject is treated with a chemotherapeutic agent.

It will easily be conceived that when the said subject is not treated with a chemotherapeutic agent, the methods of the invention permit a prognosis of the responsiveness/non responsiveness of the said subject. Thus, in this embodiment, the method of the invention allows the person skilled in the art to prognose (i.e. to identify) the subjects susceptible of responding to the chemotherapeutic agent treatment. This is important because of the destructive and potentially fatal nature of colorectal cancer and the societal costs of inefficacious chemotherapeutic treatments. Moreover, since this embodiment of the invention allows for identification of non responsive subjects before any treatment is initiated, the risks for one treated subject to encounter severe adverse effects are greatly diminished.

When the subject according to the invention is treated with a chemotherapeutic agent, the methods of the invention are useful for diagnosing if a subject responds to the said chemotherapeutic agent, and whether the said subject would thus benefit from a continuation of the said treatment. Moreover, they are useful for diagnosing subjects who are not responding to the treatment, i.e. who are refractory to the chemotherapeutic agent, and should thus swiftly shifted to another therapy. In regard of the potentially lethal nature of colorectal cancer, this achievement is crucial.

A "biological sample" may be any sample that may be taken from a subject, such as a serum sample, a plasma sample, a urine sample, a blood sample, a lymph sample, or a colorectal cancer sample. Such a sample must allow for the determination of the expression levels of OLFM4. Preferred biological samples for the determination of OLFM4 expression level by detection of the secreted olfactomedin 4 protein include samples such as a blood sample, a plasma sample, a lymph sample, or a colorectal cancer sample.

Preferably, the biological sample is a blood sample. Indeed, such a blood sample may be obtained by a completely harmless blood collection from the patient and thus allows for a non-invasive diagnosis of a chemotherapeutic agent responding or non-responding phenotype. A "biological sample" as used herein also includes a colorectal cancer sample of the patient to be tested. Such colorectal cancer sample allows the skilled person to perform any type of measurement of the level of OLFM4 and/or olfactomedin 4. In some cases, the methods according to the invention may further comprise a preliminary step of taking a colon cancer sample from the patient. By a "colorectal cancer sample", it is referred to a tumor colon tissue sample. Even in a cancer patient, colon tissue still comprises non tumor healthy tissue. The "colorectal cancer sample" should thus be limited to tumor colon tissue taken from the patient. Said "colorectal cancer sample" may be a biopsy sample or a sample taken from a surgical colon resection or a colorectal metastasis surgical resection. "Colorectal cancer sample" as used herein encompasses both colorectal primary tumors and colorectal metastatic tumors.

The amount of nucleic acid transcripts can be measured by any technology known by a man skilled in the art. In particular, the measure may be carried out directly on an extracted messenger RNA (mRNA) sample, or on retrotranscribed complementary DNA (cDNA) prepared from extracted mRNA by technologies well known in the art. From the mRNA or cDNA sample, the amount of nucleic acid transcripts may be measured using any technology known by a person skilled in the art, including nucleic microarrays, quantitative PCR, and hybridization with a labelled probe.

Therefore, the methods according to the invention may comprise another preliminary step, between the taking of the sample from the patient and steps a) as defined above, corresponding to the transformation of the colorectal cancer sample (and optionally of the healthy colon tissue sample) into a mRNA (or corresponding cDNA) sample or into a protein sample, which is then ready to use for in vitro measuring of genes expression levels in step a). Preparation or extraction of mRNA (as well as retrotranscription into cDNA) or proteins from a tissue sample is only routine procedure well known to those skilled in the art.

Once a ready-to-use colorectal cancer mRNA (or corresponding cDNA) or protein sample is available, the measure of OLFM4 gene expression levels may be performed, depending on the type of transformation and the available ready-to-use sample, either at the mRNA (i.e. based on the mRNA content of the sample) or at the protein level (i.e. based on the protein content of the sample). In some embodiments, the expression levels of some of the genes may be measured at the mRNA level, while the expression levels of other genes are measured at the protein level. In this case, part of the colorectal cancer sample taken from the patient has been transformed into an mRNA (or corresponding cDNA) sample and another part has been transformed into a protein sample. In other embodiments, the expression levels of all tested genes are measured either at the mRNA or at the protein level.

In a preferred embodiment, the expression level is determined using quantitative PCR. Quantitative, or real-time, PCR is a well known and easily available technology for those skilled in the art and does not need a precise description.

In a particular embodiment, which should not be considered as limiting the scope of the invention, the determination of the expression level using quantitative PCR may be performed as follows. Briefly, the real-time PCR reactions are carried out using the TaqMan Universal PCR Master Mix (Applied Biosystems). 6 μL cDNA is added to a 9 μL PCR mixture containing 7.5 μL TaqMan Universal PCR Master Mix, 0.75 μL of a 20× mixture of probe and primers and 0.75 μL water. The reaction consisted of one initiating step of 2 min at 50 deg. C., followed by 10 min at 95 deg. C., and 40 cycles of amplification including 15 sec at 95 deg. C. and 1 min at 60 deg. C. The reaction and data acquisition can be performed using the ABI PRISM 7900 Sequence Detection System (Applied Biosystems). The number of template transcript molecules in a sample is determined by recording the amplification cycle in the exponential phase (cycle threshold or $C_T$), at which time the fluorescence signal can be detected above background fluorescence. Thus, the starting number of template transcript molecules is inversely related to $C_T$.

In another preferred embodiment, the expression level is determined by the use of a nucleic microarray.

According to the invention, a "nucleic microarray" consists of different nucleic acid probes that are attached to a substrate, which can be a microchip, a glass slide or a microsphere-sized bead. A microchip may be constituted of polymers, plastics, resins, polysaccharides, silica or silica-based materials, carbon, metals, inorganic glasses, or nitrocellulose. Probes can be nucleic acids such as cDNAs ("cDNA microarray") or oligonucleotides ("oligonucleotide microarray"), and the oligonucleotides may be about 25 to about 60 base pairs or less in length.

Alternatively, any known or future technology permitting to assess genes expression levels based on mRNA contents may be used. For instance, tissue microarrays coupled to fluorescent in situ hybridization may be used. Tissue microarrays (also known as TMAs) consist of paraffin blocks in which up to 1000 separate tissue cores are assembled in array fashion to allow multiplex histological analysis. In the tissue microarray technique, a hollow needle is used to remove tissue cores as small as 0.6 mm in diameter from regions of interest in paraffin-embedded tissues such as clinical biopsies or tumor samples. These tissue cores are then inserted in a recipient paraffin block in a precisely spaced, array pattern. Sections from this block are cut using a microtome, mounted on a microscope slide and then analyzed by any method of standard histological analysis. Each microarray block can be cut into 100-500 sections, which can be subjected to independent tests. Tests commonly employed in tissue microarray include immunohistochemistry, and fluorescent in situ hybridization. For analysis at the mRNA level, tissue microarray technology may be coupled to fluorescent in situ hybridization.

When expression levels are measured at the protein level, it may be notably performed using specific antibodies, in particular using well known technologies such as cell membrane staining using biotinylation or other equivalent techniques followed by immunoprecipitation with specific antibodies, western blot, ELISA or ELISPOT, antibodies microarrays, or tissue microarrays coupled to immunohistochemistry. Other suitable techniques include FRET or BRET, single cell microscopic or histochemistery methods using single or multiple excitation wavelength and applying any of the adapted optical methods, such as electrochemical methods (voltametry and amperometry techniques), atomic force microscopy, and radio frequency methods, e.g. multipolar resonance spectroscopy, confocal and non-confocal, detection of fluorescence, luminescence, chemiluminescence, absorbance, reflectance, transmittance, and birefringence or refractive index (e.g., surface plasmon resonance, ellipsometry, a resonant mirror method, a grating coupler waveguide method or interferometry), cell ELISA, flow cytometry, radioisotopic, magnetic resonance imaging, analysis by polyacrylamide gel electrophoresis (SDS-PAGE); HPLC-Mass Spectroscopy; Liquid Chromatography/Mass Spectrometry/Mass Spectrometry (LC-MS/MS)). All these techniques are well known in the art and need not be further detailed here. These different techniques can be used to measure the bulk of olfactomedin 4 levels, but also, as is apparent to the skilled person, the distinct amounts of the glycosylated and non glycosylated forms. For example, the glycosylated and the non glycosylated forms of the olfactomedin 4 protein can be assessed on the basis their respective different electrophoresis mobility by Western blotting with an antibody recognizing both forms. One example of such an assay is shown in the experimental examples. Alternatively, the total amount of olfactomedin 4 protein can be assessed by ELISA with an antibody recognizing both forms, and the fraction of glycosylated olfactomedin with an antibody specific for this form. It is immediately clear that protein levels can be measured directly in a colorectal cancer sample, since it affords the skilled person to assay both the glycosylated and the non glycosylated forms. Nonetheless, as explained hereabove, it is also obvious that the level of secreted olfactomedin 4 protein can alternatively be determined from a blood sample.

The comparison of the expression levels of the measured genes in said patient's colorectal cancer sample is made by calculating an expression level ratio of the expression level of the OLFM4 gene to the expression level of a reference gene in said patient's colon cancer sample, and by comparing the obtained expression level ratio to a corresponding threshold value. Said reference gene, according to the present invention, is a gene which is expressed in all cell types. More specifically, the reference gene according to the invention is a gene which is expressed in all the cells constituting the colon. In another aspect, the expression level of the reference gene is not affected by the state of the cell, i.e. the control gene is expressed to the same level in a healthy cell and in a tumor cell. In a specific embodiment, the reference gene is a housekeeping gene. A housekeeping gene is a gene expressed in all cell types, which provides a basic function needed for sustenance of all cell types. A list of human housekeeping genes may be found in Eisenberg et al. (*Trends in Genetics* 19: 362-365, 2003). A preferred housekeeping gene according to the invention is a gene selected in the group consisting of B2M, TFRC, YWHAZ, RPLO, 18S, GUSB, UBC, TBP, GAPDH, PPIA, POLR2A, ACTB, PGK1, HPRT1, IPO8 and HMBS.

According to the present invention, a "threshold value" is intended to mean a value that permits to discriminate samples in which the expression level ratio of the gene of interest corresponds to an expression level of said gene of interest in the patient's colon cancer sample that is low or high. In particular, if a gene expression level ratio is inferior or equal to the threshold value, then the expression level of this gene in the patient's colon cancer sample is considered low, whereas if a gene expression level ratio is superior to the threshold value, then the expression level of this gene in the patient's colon cancer sample is considered high. For each gene, and depending on the method used for measuring the expression level of the genes, the optimal threshold value may vary. However, it may be easily determined by a skilled artisan based on the analysis of several control colorectal cancer samples in which the expression level (low or high)

is known for this particular gene, and on the comparison thereof with the expression of a control gene, e.g. a housekeeping gene.

The present invention further relates to a microarray dedicated to the implementation of the methods according to the invention, comprising at most 500, preferably at most 300, at most 200, more preferably at most 150, at most 100, even more preferably at most 75, at most 50, at most 40, at most 30, at most 20, at most 10 distinct probes, at least 1 of which specifically binds to OLFM4 mRNA (or corresponding cDNA) or protein.

In a preferred embodiment, said microarray is a nucleic acid microarray, comprising at most 500, preferably at most 300, at most 200, more preferably at most 150, at most 100, even more preferably at most 75, at most 50, at most 40, at most 30, at most 20, at most 10 distinct probes (thus excluding for instance pangenomic microarrays), at least 1 of which specifically hybridizes to OLFM4 mRNA (or corresponding cDNA). Said microarray may also contain at least one probe which specifically hybridizes to a housekeeping gene in addition to the probe specifically hybridizing to OLFM4. In one embodiment, said housekeeping gene is selected in the group consisting of B2M, TFRC, YWHAZ, RPLO, 18S, GUSB, UBC, TBP, GAPDH, PPIA, POLR2A, ACTB, PGK1, HPRT1, IPO8 and HMBS. More preferentially, the housekeeping gene is the IPO8 or the HMBS gene. According to the invention, a "nucleic microarray" consists of different nucleic acid probes that are attached to a substrate, which can be a microchip, a glass slide or a microsphere-sized bead. A microchip may be constituted of polymers, plastics, resins, polysaccharides, silica or silica-based materials, carbon, metals, inorganic glasses, or nitrocellulose. Probes can be nucleic acids such as cDNAs ("cDNA microarray") or oligonucleotides ("oligonucleotide microarray", the oligonucleotides being about 25 to about 60 base pairs or less in length).

Alternatively, in another embodiment, said microarray may be a protein microarray. Preferably, said microarray is an antibodies microarray, comprising at most 500, preferably at most 300, at most 200, more preferably at most 150, at most 100, even more preferably at most 75, at most 50, at most 40, at most 30, at most 20, at most 10 distinct antibodies, at least 1 of which specifically bind to olfactomedin 4 protein. Said microarray may also contain at least one antibody which specifically binds to a housekeeping protein, in addition to the antibody specifically binding to the olfactomedin 4 protein. In one embodiment, said housekeeping protein is selected in the group consisting of the B2M, TFRC, YWHAZ, RPLO, 18S, GUSB, UBC, TBP, GAPDH, PPIA, POLR2A, ACTB, PGK1, HPRT1, IPO8 and HMBS proteins. In a preferred embodiment, said housekeeping protein is the IPO8 or HMBS protein.

Alternatively to nucleic acid or antibody microarray technology, quantitative PCR may be used and amplification primers specific for the genes to be tested are thus also very useful for performing the methods according to the invention. The present invention thus further relates to a kit for diagnosing the presence of a KRAS mutation in a colorectal cancer in a patient from a colorectal cancer sample of said patient, comprising at least one reagent for the determination of the OLFM4 expression level. The invention also relates to a kit for the in vitro diagnosis of a responding or non responding phenotype, comprising at least one reagent for the determination of the OLFM4 expression level. In a specific embodiment, the kit of the invention comprises a dedicated microarray as described above or amplification primers specific for OLFM4. Here also, when the kit comprises amplification primers, while said kit may comprise amplification primers specific for other genes, said kit preferably comprises at most 100, at most 75, 50, at most 40, at most 30, preferably at most 25, at most 20, at most 15, more preferably at most 10, at most 8, at most 6, even more preferably at most 5, at most 4, at most 3 or even 2 or one or even zero couples of amplification primers specific for other genes than OLFM4. For example, said kit may comprise at least a couple of amplification primers for at least one housekeeping gene in addition to the primers for OLFM4. In one embodiment, said housekeeping gene is selected in the group consisting of B2M, TFRC, YWHAZ, RPLO, 18S, GUSB, UBC, TBP, GAPDH, PPIA, POLR2A, ACTB, PGK1, HPRT1, IPO8 and HMBS. In a preferred embodiment, said housekeeping gene is the IPO8 or HMBS gene.

The practice of the invention employs, unless other otherwise indicated, conventional techniques or protein chemistry, molecular virology, microbiology, recombinant DNA technology, and pharmacology, which are within the skill of the art. Such techniques are explained fully in the literature. (See Ausubel et al., *Current Protocols in Molecular Biology, Eds.*, John Wiley & Sons, Inc. New York, 1995; Remington's Pharmaceutical Sciences, 17th ed., Mack Publishing Co., Easton, Pa., 1985; and Sambrook et al., Molecular cloning: A laboratory manual 2nd edition, Cold Spring Harbor Laboratory Press—Cold Spring Harbor, N.Y., USA, 1989). Unless defined otherwise, all technical and scientific terms used herein have the same meaning as is commonly understood by one of the skill in the art to which this invention belongs.

Having generally described this invention, a further understanding of characteristics and advantages of the invention can be obtained by reference to certain specific examples and figures which are provided herein for purposes of illustration only and are not intended to be limiting unless otherwise specified.

FIGURE LEGENDS

FIG. 1: iTRAQ workflow

Figure 2:
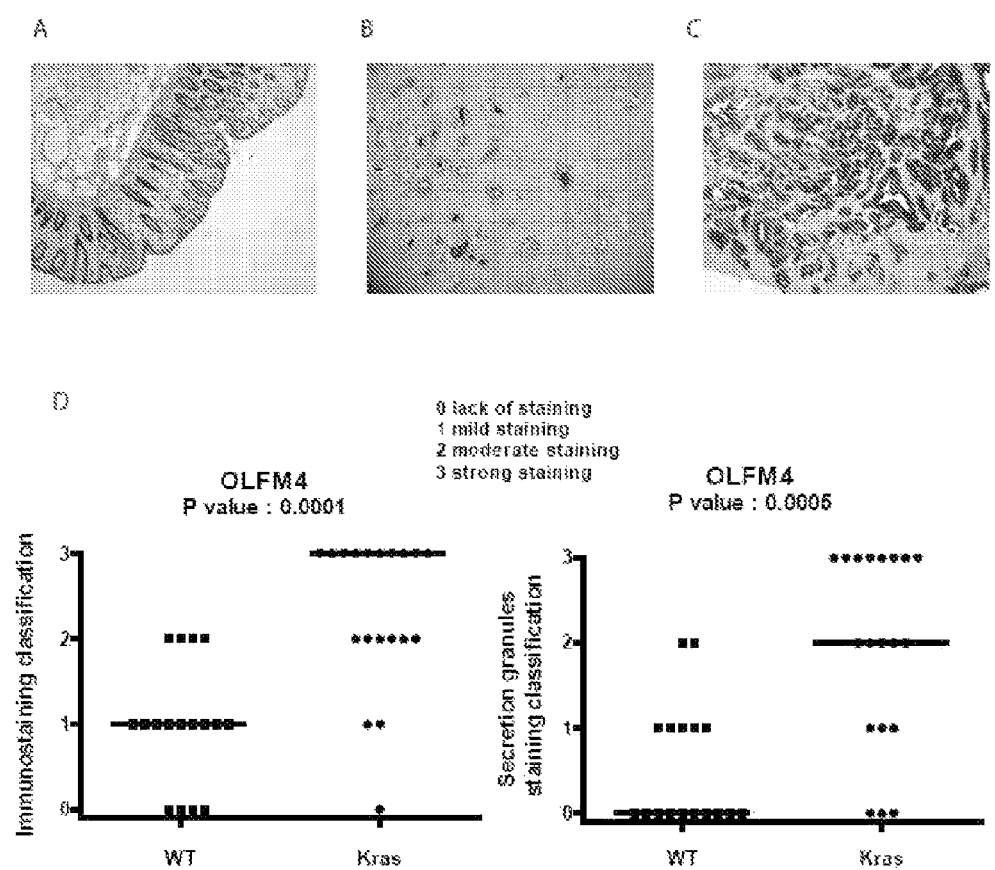

FIG. 2: OLFM4 is overexpressed in KRAS tumors.

Immunohistochemical analysis of OLFM4 was performed in colon tissues. In the normal colon tissue (A), a moderate staining was observed in the crypts, whereas the surface epithelium stained negative. In the KRAS tumor tissue (B), the staining is very strong whereas the staining in WT tumor tissue (C) is lower.

Figure 3:
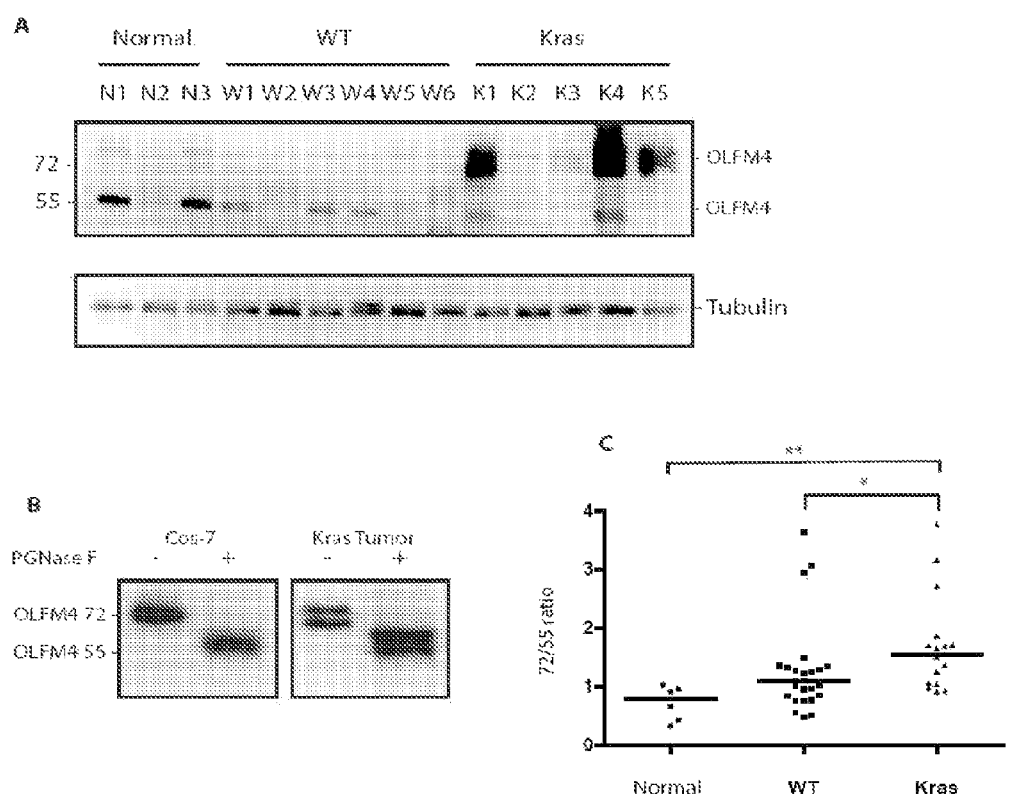

FIG. 3: OLFM4 is glycosylated in KRAS tumors.

A. Total extracts form normal and tumor tissues were realized by X buffer. The western Blot analysis against OLFM4 was performed to detect native and glycosylated OLFM4 in control, WT and KRAS tissues. B. Deglycosylation analysis of OLFM4: OLFM4 was significantly secreted from the COS-7 cells; the secreted form at 72 kDa was treated with (+) or (−) PNGase F. The size of deglycosylated OLFM4 is consistent with the molecular mass of calculated OLFM4 gene product. Treatment of 72 kDa band in KRAS tumor leads to the same band at 55 kDa. C. The ratio between 72 and 55 kDa bands were calculated for normal tissues, WT and KRAS tumor tissues. The expression of glycosylated OLFM4 is significantly higher in KRAS tumor in comparison with normal tissues (p=0.002) and to WT tissues (p=0.011).

Figure 4:
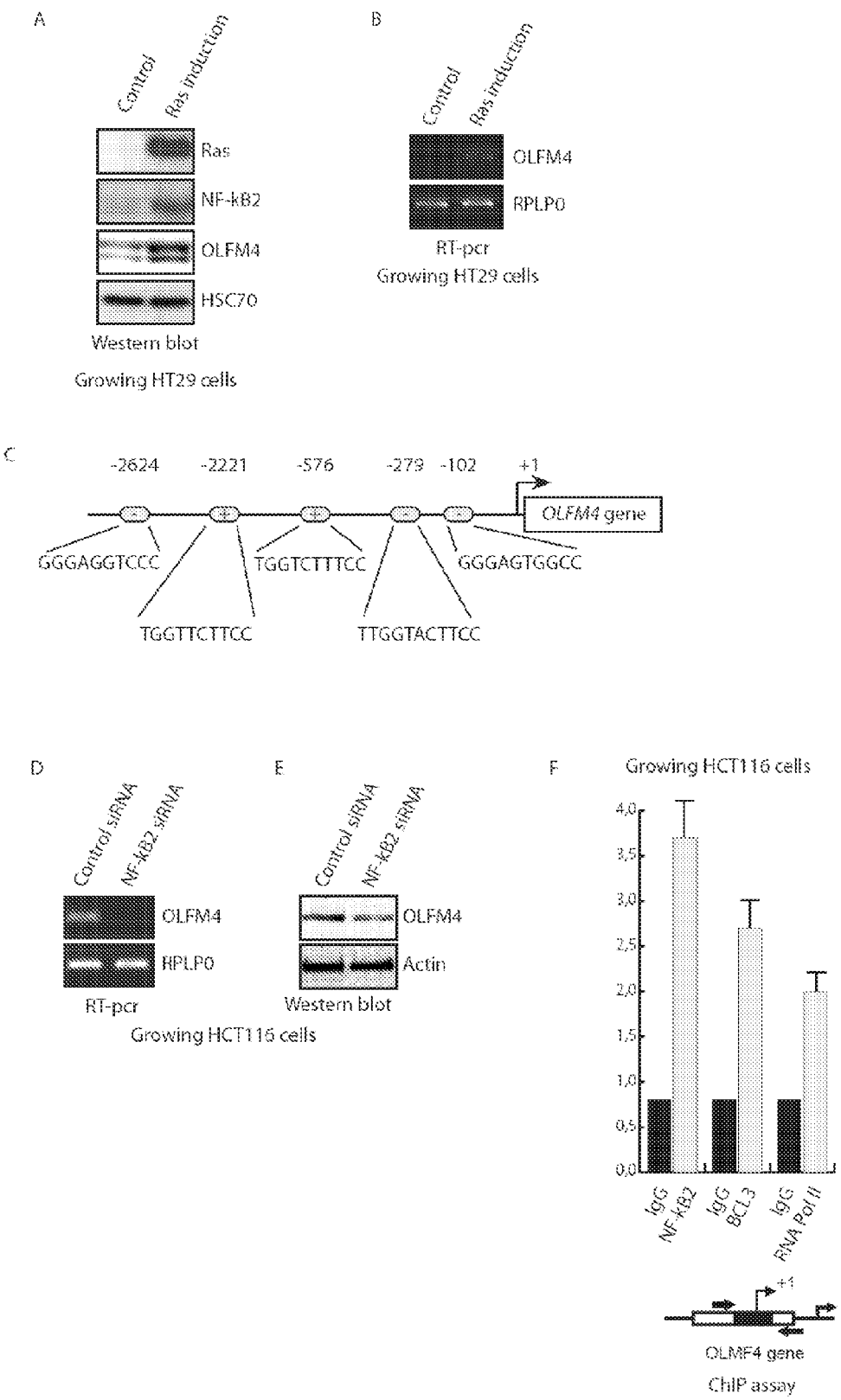

FIG. 4: NF-κB2 regulates OLFM4 expression following Ras induction.

A. HT29-H-RasV12 colorectal cell lines were treated or not with doxycyclin for the indicated time, whole cell extracts were prepared and analyzed using antibodies directed against Ras, NF-κB2, OLFM4 and HSP70. B. Cells were treated as above and the mRNA expressions of OLFM4 and RPLPO were evaluated by semi-quantitative RT-PCR. C. Schematic representation of the potential NF-κB binding sites of the OLFM4 promoter. The reading frame of the binding site is indicated by + for 5'-3' and − for 3'-5'. D-E. HCT116 colorectal cell lines were either transfected with NF-κB2 specific or control siRNA oligonucleotides as indicated. The mRNA extracts (D) and whole cell extracts (E) were processed and the OLFM4 expression was analyzed 48 hr after siRNA transfection. F. Soluble chromatin from growing HCT116 cells was prepared and immunoprecipitated with antibodies targeted against NF-κB2, Bcl3 and the RNA polymerase II. DNA was amplified using pair of primers that cover the NF-κB proximal binding site of the OLFM4 promoter. ChIP assays were then quantified by real-time RT-PCR as compared to the signal obtained on a control sequence with a control IgG.

Figure 5:
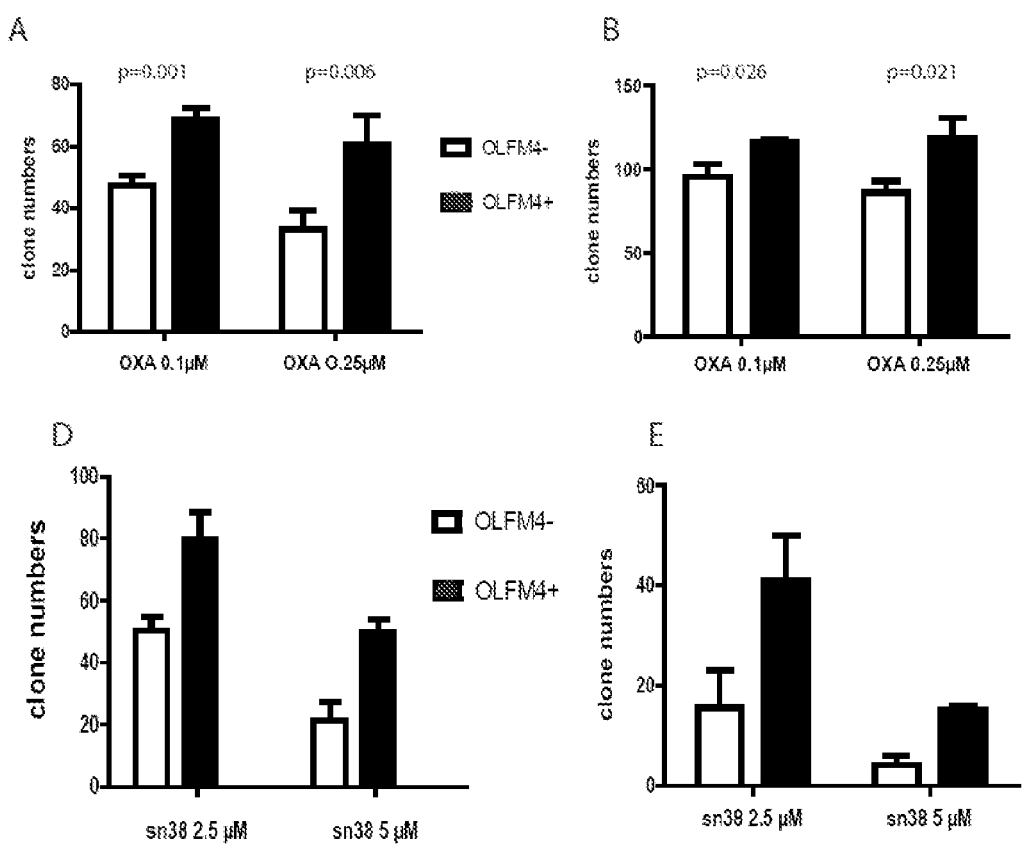

FIG. 5: Secreted OLFM4 induces resistance to oxaliplatin and sn38 in colorectal cells.

The influence of OLFM4 following genotoxic treatments in HCT116 OLFM4 inducible cells was evaluated by clonogenic assay. Cells were incubated with 50 ng/ml of doxycyclin, and then 24 hr later treated with oxaliplatin or sn38 at the indicated concentration for 10 days. The colonies were stained with crystal violet and counted by QuantityOne software (Biorad). B. OLFM4 overexpressed in COS7 cells, was added at approximately 3 ng/ml to oxaliplatin and sn38 treatment in the wild type HCT116 cells for 10 days. The colonies were stained and count as above. The histograms shown are representative of three individual experiments.

EXPERIMENTAL EXAMPLES

Materials and Methods

Cell Line:

The human colon adenocarcinoma cell line HCT116 (American Type Culture Collection, ATCC) were maintained in antibiotic-free RPMI 1640 medium (Lonza). Cultures were supplemented with 10% fetal bovine serum. Cell lines were maintained at 37° C. in 5% CO2 and were tested to rule out mycoplasma contamination.

Cell Culture and Stable Transfection:

The plasmid pCMV/OLFM4 (Imagenes) was stably co-transfected with the pcDNA6/TR using LipofectAMINE 2000 reagent (Invitrogen) according to the manufacturer's instruction. HCT116 stable cells lines were selected with 100 μg·mL$^{-1}$ blasticidin (Sigma Aldrich, Deisenhofen, Germany) and 800 μg·ml$^{-1}$ G418 for 1 month and maintained in RPMI 1640 medium supplement with 10% fetal bovine serum containing 5 μg·ml$^{-1}$ blasticidin and 200 μg·ml$^{-1}$ G418 OLFM4 expression was induced by 50 ng·ml$^{-1}$ doxycycline for 48 h. The expression of OLFM4 protein in these stable cell lines was confirmed by Western blot as previously described.

Clonogenic Cell Survival Assay:

HCT116 stable OLFM4 cells were seeded at 300 cells into 6 well cell culture plates with RPMI 1640 medium supplement with 3% fetal bovine serum and incubated at 37° C. in a 5% $CO_2$ atmosphere. Cells were then induced with 50 ng·mL$^{-1}$ doxycycline (Sigma) for 24 h. After, the cells were traited with SN38 and Oxaliplatine and incubated at 37° C. in a 5% $CO_2$ atmosphere for 10 days, washed twice with PBS and stained with 0.1% crystal violet. The number of colonies exceeding 50 cells was visualized with a Bio-Rad Chemi Doc XRS Imaging device and counted using Quantity One imaging software (Bio-Rad). The survival fraction was determined as the ratio of the number of colonies observed without doxycycline to the number of cells with doxycycline, adjusted to the plating efficiency.

Laser Capture Microdissection (LCM):

Frozen sections (12 μm thick) of either colon cancer or normal colonic mucosa were cut on a cryostat (Bright instrument Co Ltd, St Margarets Way, UK). The sections were then stained with toluidine blue using a rapid staining method. Toluidine blue stained sections were also prepared for visual reference. The tissue sections were put in the 70% ethanol bath for 1 minute, 95% ethanol for 2 minutes, 95% ethanol for 2 minutes, and finally, twice bath in 100% xylene for 5 minutes. Xylene was allowed to evaporate completely from the sections and then the sections were microdissected using a PixCell II laser capture microdissection system (Arcturus Engineering, Mountain View, Calif., USA).

The laser capture system was equipped with PixCell II image archiving software (Arcturus Engineering). The settings of the laser were as follows: spot diameter set at 7.5 μm, pulse duration 70 milliseconds, and power 70 mW. After microdissection, the plastic film containing the microdissected cells was removed and all the films containing material from a single sample placed in a microcentrifuge tube DNA extraction and protein lysis solution added. Approximately 30,000 cells were captured from a single or consecutive tissue sections using up to 5 CapSure LCM Caps (Molecular Devices Corporation), which were transferred to a 0.5 ml sterile Eppendorf tube for protein extraction (see below).

Pyrosequencing Analysis:

Genomic DNA from frozen tissue was extracted with the PicoPure™ DNA extraction kit (Arturus Bioscience, Inc. Mountain View, Calif., USA) and a whole genome amplification of genomic DNA was performed by polymerase chain reaction (PCR) using random 15-mer primers.

Biotinylated PCR products were performed with an initial denaturation at 95° C. for 5 min, followed by 35 cycles of denaturation at 95° C. for 30 s, primer annealing at 54° C. for 30 s, and extension at 72° C. for 1 min, followed by a final extension for 5 min at 72° C. All amplification reactions were performed in a DNAThermal Cycler 480 (Perkin Elmer, Boston, USA) with 1 unit of Taq Polymerase (Euroblue Taq-Eurobio, Les Ulis, France). The different sets of primers used to amplify the sequences of interest were: PCR primer sequences by KRAS mutation for codons 12-13 (sense) 5'-AAC CTT ATG TGT GAC ATG TTC T-3' (SEQ ID NO. 1), (antisense): 5'-biotin-TCG TCC ACA AAA TGA TTC TGA-3' (SEQ ID NO. 2) and Sense Sequencing primer: 5'-CTT GTG GTA GTT GGA GC-3' (SEQ ID NO. 3) Codon 61: primer sequence: (sense): 5'-TTA TGG CAA ATA CAC AAA GAA AGC-3' (SEQ ID NO. 4), (antisense): 5'-biotin-CAG ACT GTG TTT CTC CCT TCT CA-3' (SEQ ID NO. 5) and Sense Sequencing primer 5'-ATA TTC TCG ACA CAG CAG-3' (SEQ ID NO. 6). Different sequencing primers were designed to carry out KRAS gene pyrosequencing analysis. A selection was then made according to their ability to provide interpretable Pyrograms™. DNA products consisted of amplified genomic DNA from control subjects.

Mutations in the exon 1 fragment of the KRAS gene were detected by direct sequencing of the PCR fragment without any need for further purification with the Pyrosequencer PyroMark ID system (Biotage AB and Biosystems, Uppsala, Sweden). For Pyrosequencing, ssDNA was prepared from 40 µl biotinylated PCR product using streptavidin-coated sepharose, and 1.5 pmol of the sequencing primer was used for analysis. Sequencing was performed with the SNP Reagent Kit (Biotage) according to the manufacturer's instructions.

Protein Extraction and Digestion:

Protein extraction was carried out using the Liquid Tissue MS Protein Prep kit according to manufacturer's protocol (Expression Pathology Inc., Gaithersburg, Md., USA). Briefly, the films from the underside of the caps for each sample were removed, transferred to low binding reaction tubes, and incubated with 20 µL of Liquid Tissue extraction and heated at 95° C. for 90 minutes. After cooling for 2 minutes on ice, 5 µL of trypsin reagent was added and incubated at 37° C. for one hour with vigorous shaking for 30 second at 20 minute intervals. Samples were further incubated overnight at 37° C. followed by heating at 95° C. for 5 minutes.

In preparation for labeling, the samples were harvested via centrifugation at 10,000 g, dried completely using a Speed-Vac and re-suspended in 100 µl of 0.5% trifluoroacetic acid (TFA) in 5% acetonitrile, and were desalted via PepClean C-18 spin columns (Pierce Biotechnology, Rockford, Ill.) and dried for iTRAQ™ processing.

Peptide Labeling with iTRAQ Reagents:

Peptides samples were resuspended with 30 µL of iTRAQ dissolution buffer (Applied Biosystems) and were reduced with 5 mM Tris-(2-carboxyethyl)phosphine (TCEP) at 60° C. for 1 h and the cysteine-groups were blocked using a 10 mM methyl methanethiosulfonate (MMTS) solution at room temperature for 10 min. Each peptide solution was labeled at room temperature for 2 h with one iTRAQ reagent vial (mass tag 114, 115, 116 or 117) previously reconstituted with 70 µL of ethanol. A mixture containing small aliquots from each labeled sample was analyzed by MS/MS to determine a proper mixing ratio to correct for unevenness in peptide yield from Liquid Tissues procedures. Labeled peptides were then mixed in 1:1:1:1 ratio. Peptide mixture was then dried completely using a Speed-Vac.

Peptide OFFGEL Fractionation:

For pI-based peptide separation, we used the 3100 OFFGEL Fractionator (Agilent Technologies, Böblingen, Germany) with a 24-well set-up. Prior to electrofocusing, samples were desalted onto a Sep-Pak C18 cartridge (Waters). For 24-well set-up, peptide samples were diluted to a final volume of respectively 3.6 mL using OFFGEL peptide sample solution. To start, the IPG gel strips of 24 cm-long (GE Healthcare, München, Germany) with a 3-10 linear pH range was rehydrated with the Peptide IPG Strip Rehydradation Solution according to the protocol of the manufacturer for 15 min. Then, 150 µL of sample was loaded in each well. Electrofocusing of the peptides is performed at 20° C. and 50 µA until the 50 kVh level was reached. After focusing, the 24 peptide fractions were withdrawn and the wells rinsed with 200 µL of a solution of water/methanol/formic acid (49/50/1); after 15 min, the rinsing solutions were pooled with their corresponding peptide fraction. All fractions were evaporated by centrifugation under vacuum and maintained at −20° C. Just prior nano-LC, the fractions were resuspended in 20 µL of H2O with 0.1% (v/v) TFA.

Capillary LC Separation:

The samples were separated on an Ultimate 3,000 nano-LC system (Dionex, Sunnyvale, USA) using a C18 column (PepMap100, 3 µm, 100A, 75 µm id×15 cm, Dionex) at a flow rate of 300 nL/min. Buffer A was 2% ACN in water with 0.05% TFA and buffer B was 80% ACN in water with 0.04% TFA. Peptides were desalted for 3 min. using only buffer A on the precolumn, followed by a separation for 105 min. using the following gradient: 0 to 20% B in 10 min, 20% to 45% B in 85 min and 45% to 100% B in 10 min. Chromatograms were recorded at the wavelength of 214 nm. Peptide fractions were collected using a Probot microfraction collector (Dionex). We used CHCA (LaserBioLabs, Sophia-Antipolis, France) as MALDI matrix. The matrix (concentration of 2 mg/mL in 70% ACN in water with 0.1% TFA) was continuously added to the column effluent via a micro "T" mixing piece at 1.2 µL/min flow rate. After 12 min run, a start signal was sent to the Probot to initiate fractionation. Fractions were collected for 10 s and spotted on a MALDI sample plate (1,664 spots per plate, Applied Biosystems, Foster City, Calif.).

MALDI-MS/MS:

MS and MS/MS analyses of off-line spotted peptide samples were performed using the 4800 MALDI-TOF/TOF Analyser (Applied Biosystems). After screening of all LC-MALDI sample positions in MS-positive reflector mode using 1500 laser shots, the fragmentation of automatically-selected precursors was performed at collision energy of 1 kV using air as collision gas (pressure of ~2×10-6 Torr). MS spectra were acquired between m/z 800 and 4000. For internal calibration, we used the parent ion of Glu1-fibrinopeptide at m/z 1570.677 diluted in the matrix (3 femtomoles per spot). Up to 12 of the most intense ion signals per spot position having an S/N>12 were selected as precursors for MS/MS acquisition. Peptide and protein identification were performed by the ProteinPilot™ Software V 3.0 (Applied Biosystems) using the Paragon algorithm. Each MS/MS spectrum was searched for *Homo sapiens* specie against the Uniprot/swissprot database.

The searches were run using with the fixed modification of methylmethanethiosulfate labeled cysteine parameter enabled. Other parameters such as tryptic cleavage specificity, precursor ion mass accuracy and fragment ion mass accuracy are MALDI 4800 built-in functions of ProteinPilot software.

Quantification of Relative Protein Expression:

We employed a customized software package, iQuantitator, to infer the magnitude of change in protein expression. The software infers treatment-dependent changes in expression using Bayesian statistical methods. Basically, this approach was used to generate means, medians, and 95% credible intervals (upper and lower) for each treatment-dependent change in protein expression by using peptide-level data for each component peptide, and integrating data across the two experiments. For proteins whose iTRAQ ratios were downregulated in tissues, the extent of downregulation was considered further if the null value of 1 was above the upper limit of the credible interval. Conversely, for proteins whose iTRAQ ratios were up-regulated in tumors, the extent of upregulation was considered further if the lower limit of the credible interval had a value greater than 1. The width of these credible intervals depends on the data available for a given protein. Since the number of peptides observed and the number of spectra used to quantify the change in expression for a given protein are taken into consideration, it is possible to detect small but significant changes in up- or downregulation when many peptides are available.

Data from a total of 468599 spectra from two 4 iTRAQ experiments were considered using this customized software Of the total, 84628 spectra were used to identify 9286 peptides (2971 unique proteins). For each protein, and each peptide associated with a given protein, the mean, median, and 95% credible intervals were computed for each of the protein- and peptide-level treatment effects.

Western Blot Analysis of Proteins in Normal Tissues and CRC:

Whole cell lysates were prepared from three normal tissues, three cancerous tissues non-mutated of KRAS gene and three cancerous tissues mutated of KRAS gene. Frozen tissue samples were homogenized and lysed in a buffer containing 7M urea, 2M thiourea and 4% (w/v) CHAPS at 4° C. for 1 h using a rotary shaker. Lysis was achieved by sonication on ice (3×5 s pulses), and the lysates were clarified by centrifugation at 14,000×g at 4° C. for 15 min. Protein concentrations were determined using the Fluoro-Profile Protein Quantification Kit (Sigma-Aldrich Corporation), with BSA as the standard, and equal amounts of proteins (80 µg/lane) from the samples tissues were resolved on a 10% SDS polyacrylamide gel. The proteins were then electrotransferred onto PVDF membranes. After blocking with 3% BSA in TBS (0.1 M, pH=7.4), blots were incubated with the respective primary antibodies (1:200 dilution) at 4° C. overnight. The protein abundance of β-tubulin was used as a control for protein loading and was determined with rabbit polyclonal anti-β-tubulin: (H-235) antibody (sc-9104, Santa Cruz Biotechnology Inc.). Membranes were incubated with the respective secondary antibody, horseradish peroxidase-conjugated rabbit anti-IgG (goat anti-rabbit IgG, 1:5000, Santa Cruz Biotechnology Inc.), and diluted with 1% bovine serum albumin for 1 h at room temperature. After each step, blots were washed three times with 0.05% Tween, TBS. The membrane was probed with the indicated antibodies and developed with the ECL.

Immunohistochemistry:

Primary antibodies used for validation studies include: rabbit anti-Olfactomedin-4 (Cat. # ab78496, Abcam, Cambridge, Mass., 1:25), rabbit anti-β-tubulin (Cat. #, Santa Cruz Biotechnology Inc., Santa Cruz, Calif.; 1:200), rabbit A quantitative score was performed by estimating the percentage of immunopositive stained cells: 0, –10% cells; 1, 10-30% cells; 2, 30-50% cells; 3, 50-70% cells; and 4, >70% cells. Second, the intensity of staining was scored by evaluating the average staining intensity of the positive cells and secretion (0, none; 1, weak; 2, intermediate; and 3, strong). The immunohistochemical data were subjected to statistical analysis as described above for the MS results.

Deglycosylation Experiment and In Vitro Translation of OLFM4:

The purified culture media and lysate of COS-7 cells were pre-denatured in glycoprotein denaturing buffer at 100° C. for 5 min. The denatured proteins were then treated with cocktail enzymes (Sigma-Aldrich Corporation) at 37° C. for 3 h according to the manufacturer's recommendation, separated on 6% SDS-PAGE and followed by Western blot analysis. The pCMV-OLFM4 construct was transcribed and translated in the presence.

Chromatin Immunoprecipitation Assays:

Cells, grown to 60% confluence, were treated or not as indicated and then washed and cross-linked with 1% formaldehyde at room temperature for 8 min essentially as previously described (29, 30). Reaction was stopped with 10 ml of 125 mM glycin solution. Cells were washed with cold PBS and lysed in 500 µl of lysis buffer (1% SDS, 10 mM EDTA, 50 mM Tris-HCl pH 8.1, 1 mM PMSF, 5 mM NaF, 5 mM Na3VO4, 2 µg/ml leupeptin, 5 µg/ml aprotinin, 1 µg/ml pestatin), and sonicated five times for 20 seconds each. Supernatants were then recovered by centrifugation at 12 000 rpm for 10 min at 4° C., diluted once in dilution buffer (1% Triton X-100, 2 mM EDTA, 150 mM NaCl, 20 mM Tris-HCl pH 8.1) and subjected to one round of immunoclearing for 2 h at 4° C. with 2 µg of sheared salmon-sperm DNA, and 20 µl of protein G-agarose coated with salmon sperm DNA (Millipore) (of 50% slurry). Immunoprecipitation was performed overnight with specific antibodies and IgG control, and then 2 µg of sheared salmon-sperm DNA and 20 µl of protein G-agarose coated with salmon sperm DNA (Millipore) (of 50% slurry) were further added for 1 h at 4° C. Note that immunoprecipitations were performed in the presence of 1% Igepal CA-630. Immunoprecipitates were washed sequentially for 10 min each in TSE I (0.1% SDS, 1% Triton X-100, 2 mM EDTA, 20 mM Tris-HCl pH 8.1, 150 mM NaCl), TSE II (0.1% SDS, 1% Triton X-100, 2 mM EDTA, 20 mM Tris-HCl pH 8.1, 500 mM NaCl), and TP3 (250 mM LiCl, 1% NP-40, 1% deoxycholate, 1 mM EDTA, 10 mM Tris-HCl pH 8.1). Beads precipitates were then washed once with TE buffer and eluted once with 1% SDS, 100 mM NaHCO3. Eluates were heated at 65° C. for 6 hours to reverse the formaldehyde cross-linking. DNA was precipitated using classical procedures. Real-time PCR was used for ChIP analysis and quantification. The ChIP have been calculated as binding to region of interest/IgG control, divided by binding to negative control region/IgG control. The following primers were used:

Transcription initiation site of the OLFM4 promoter:

```
SEQ ID NO: 7:
For 5'-GCCATGACTCAGATTCCT-3'

SEQ ID NO. 8:
Rev 5'-CAGGGGCTTCTTATAGTG-3'
``` control region:

```
SEQ ID NO. 9:
For 5'-TGTGCAGGTGGGTGTAGTTG-3'

SEQ ID NO. 10:
Rev 5'-CCAGGCACAAGGCTAAGAGT-3'
```

Primers:

Total RNA was isolated from cell lines with TRIzol reagent (Invitrogen) and expression was measured by semi-quantitative PCR analysis using the following:

```
OLFM4:
SEQ ID NO. 11:
For 5'-TTCGCCGAGAAATCGTGGCTCT-3'

SEQ ID NO. 12:
Rev 5'-AGCTGAACCACAGACGGTTTGCT-3'

RPLP0:
SEQ ID NO. 13:
For 5'-AACCCAGCTCTGGAGAAACT-3'

SEQ ID NO. 14:
Rev 5'-CCCCTGGAGATTTTAGTGGT-3'
```

Other Assays:

DNA transfections, siRNA knockdown, RNA extraction, reverse transcription, semi-quantitative and quantitative polymerase chain reaction, protein extracts and western blots were all performed as described previously (29, 31). All experiments were performed a minimum of three times before calculating means and standard deviations as shown in figures.

Results
Genetic Analyses

From a bank of 49 primary non-treated colorectal tumors, we carried out the detection of the most common mutations occurring in colorectal tumors: k-ras, pi3k, b-raf, p53. Genetic tests were performed from microdissected tumor tissue. Among these tumors, 30 were mutated at least on one oncogene (66%) and 16 tumors (35.5%) showed mutations on the K-ras oncogene. Among these 19 tumors 3 of them are also mutated for p53 and PI3K. These results are consistent with those already published in literature. Tumors mutated on p53, Raf or PI3 kinase were excluded from this study to compare non-mutated with K-ras mutated samples.

Colorectal Tumor Protein Identification

Four iTRAQ runs (3 iTRAQ 4plex and 1 iTRAQ 8plex) were conducted from 15 microdissected colorectal tumors (FIG. 1). Since we have found isoelectric focusing immobilized pH gradient strips to be useful for complex proteome characterization, we in-solution separated the pool of iTRAQ peptides in a 24-fraction format OFFGEL apparatus. Each peptide fraction was submitted to LC-MS/MS. A total of 105,247 MS/MS spectra (with a MASCOT score>95%) were acquired over 4 iTRAQ experiments. Of these, 84,628 spectra were utilized to assign 9286 unique peptides, representing 2971 unique proteins (FDR<0.09%, with at least 2 peptides). To determine the depth of our tumor coverage, the proportion of regulatory proteins such as kinases and transcription factors was determined. A total of 124 kinases were identified. This corresponds to 4.1% of the 2971 proteins in our colorectal tumor proteome with GO annotations which is equivalent to the proportion expected from the human genome (4.1%). We identified 135 transcription factors which correspond to 4.5% of our tumor proteins and which is slightly less than the 5.4% expected from the genome. Next, GO cellular component analysis was performed and proteins were identified in several subcellular compartments such as mitochondrion, endoplasmic reticulum, nuclear part, cytosol, actin cytoskeleton, cytoplasmic vesicle, extracellular region and plasma membrane. All categories were overexpressed with respect to the genome, suggesting that our analysis detected preferentially abundant proteins Of these 2971 proteins identified in this study, we initially examined proteins which were statistically significantly differentially expressed between the pool of normal tissues and the tumors. 210 proteins with confidence interval (% CI) above 95% present in 9 tumors were identified. Among these identified proteins, 84 were overexpressed and 126 were underexpressed. Several have already been published as candidate biomarkers in the literature. According to GO annotation, 58 proteins (28%) were classified as belonging to the extracellular part of the cell (GO:0005576). These proteins were the most differentially expressed between non mutated and mutated tumors, and among those, 25 were overexpressed.

Mass Spectrum Identification of Differentially Expressed Proteins in KRAS Tumors From the KRAS mutated tumors, we characterized 223 differentially expressed proteins compared to normal tissues. 96 proteins were overexpressed and 127 were underexpressed. The first conclusion is the number of differentially expressed proteins is higher when we selected KRAS tumors.

To characterize proteins that were specifically expressed in K-ras mutated tumors as compared to their non-mutated counterparts, 3 independent iTRAQ runs were performed, comparing 6 non mutated tumors versus 6 KRAS tumors. Following statistical analyses performed on 27 tumors, results showed that two proteins were differentially expressed between the two conditions (>50%): HLA-DRA with an iTRAQ ratio KRAS/WT of 0.54 and OLFM4 with an iTRAQ ratio KRAS/WT of 1.93.

HLA-DRA

HLA-DRA (iTRAQ ratio 0.54) is one of the HLA class II alpha chain paralogues. It plays a central role in the immune system by presenting antigens derived from extracellular proteins. HLA-DRA is an inflammatory gene which has a role in colon carcinogenesis. Our result is consistent with previous study on HLA-DRA mRNA quantification which showed that HLA-DRA mRNA expression was significantly decreased in colorectal tumors from several cohorts. In our case, it should be noted that HLD-DRA expression is only significantly down-regulated in K-ras mutated tumors.

OLFM4

GW112, also known as olfactomedin 4 (OLFM4) or human G-CSF clone-1 (hGC-1), was originally cloned from human myeloid cells and encodes a secreted glycoprotein of 510 amino acids. GW112 is normally expressed in the bone marrow, intestine and prostate, and altered expression is observed in various tumors including colon, breast, and lung cancers. Recent studies have suggested that GW112 is involved in the regulation of apoptosis. When overexpressed, this protein enhanced the survival of tumor cell and favored tumor growth. In addition, the OLFM4 gene is regulated by the NF-κB transcription factor to promote cell survival in gastric cancer cell. Recently, OLFM4 was shown to be a potential gastric cancer biomarker with 25% sensitivity for stage I, 63% for stage II, 40% for stage III and 30% for stage IV with a specificity of 95%.

In our experimental conditions, OLFM4 was detected with the highest statistical confidence and we focused on this protein for the following part of the study.

Validation of OLFM4 Overexpression by Immunohistochemistry

To confirm the altered expression of olfactomedin-4 in KRAS tumor versus WT tumors and non-neoplastic colon, an immunohistochemical analysis in paraffin-embedded tissues was performed with 15 WT and 17 KRAS-mutated tumors. As reported previously, immunohistochemistry experiments showed that olfactomedin 4 was expressed in the basal crypt epithelium but not at the luminal surface of normal tissue; (FIG. 2A). In tumor tissues, olfactomedin-4 was detected only in the cytoplasm or in the secretion vesicles but never in the stroma. This observation suggests that OLFM4 overexpression is not due to the inflammatory response observed in the surrounding stroma. The comparison between WT and KRAS tissues were investigated with two criteria: the immunostaining of the tumor cells and the immunostaining of the secretion vesicles. For cytoplasmic localization of olfactomedin-4 in tumor cells, in the non-mutated specimens, no staining was detected in 27% (4 of 15), a weak staining was detected in 47% (7 of 15) and a moderate staining was observed in 27% of the tumors (4 of 15) (FIG. 2B). In the KRAS-mutated tumors, no staining was detected in 5% (1 of 17), a weak OLFM4 staining was detected in 11% (2 of 17), a moderate staining was detected in 35% (6 of 17) and a strong staining was detected in 47% of the tumors (8 of 17) (FIG. 2C). As shown in FIG. 2, significant differences in staining intensity and positive cells were observed among WT and KRAS tissues. For the localization in secretion vesicles, in the WT tissues, no staining was exhibited for the majority of our specimen with 67% (10 of 15), mild staining was detected for 20% (3 of 15) and moderate staining was detected for 13% of the tumors (2 of 15); in the KRAS-mutated tissues, no staining was detected in 17% (3 of 17), a weak staining was detected in 17% (3 of 17), moderate staining was detected in 29% (5 of 17) and strong staining was detected in 35% of the tumors (6 of 17). The results reported in FIG. 2D show a significant difference in staining classification between WT and KRAS tissues indicating that overexpression of glycosylated olfactomedin-4 was correlated with KRAS mutations in colon tumors.

Validation of OLFM4 Overexpression by Western Blotting

The differential expression of olfactomedin-4 was also verified by Western blot analysis. Western blot assay was performed on 22 independent colorectal tumors (11 wild type and 11 KRAS). As shown in FIG. 3A, two bands were detected, one at the expected molecular mass at 55 kDa and another band around 72 kDa, suggesting that this protein is modified by glycosylation. To verify this hypothesis, protein samples were incubated with deglycosylating enzymes (PN-Gase F). Following incubation, a shift in the molecular weight from 72 kDa to 55 kDa was observed, indicating that the protein is effectively modified by N-glycosylation, as recently described for OLFML1, a different member of olfactomedin family.

OLFM4 is a Highly Glycosylated Secreted Protein

To determine whether OLFM4 is secreted into extracellular medium, a vector expressing the OLFM4 cDNA was transiently transfected into COS-7 cells. Culture media and cell lysates were collected 72 hr after transfection, and analyzed by Western blot. The resulting data showed that OLFM4 was detected in both culture medium and cell lysate (FIG. 3B). This result further suggests that OLFM4 is exported into the extracellular medium as a secreted protein. Note that only the 72 kDa form was detected in the supernatant, indicating that this protein is secreted as a glycosylated protein. To determine if the endogenous OLFM4 could also be found as a secreted protein, its presence was analyzed in the supernatants of two human colorectal cell lines, HCT116 and HT29. The protein was effectively detected, secreted at 72 kDa.

Overexpression of Glycosylated Olfactomedin-4 was Correlated with KRAS Tumors

The western blot assay (FIG. 3A) suggested that the glycosylated olfactomedin-4, expressed as a 72 kDa isoform, was specific of K-ras mutated tumors and was not present in non-mutated tumors. To confirm this observation, we selected 43 independent tumors (26 WT and 17 KRAS) and 6 healthy controls for a second western blot assay. We calculated for each tissue the ratio between the 72 kDa and 54 kDa bands, which illustrates the ratio between the secreted form and the intracellular olfactomedin-4. In healthy patients, the band at 72 kDa is always present, thus explaining the basal rate on the olfactomedin-4 in human serum; nevertheless, the ratio 72/55 always indicated a higher expression of the intracellular olfactomedin-4 with a median value of 0.72. In WT tumors, the median was at 1.27 and not significantly higher than that in healthy control. By contrast, in KRAS tumors, the ratio 72/55 rose to 1.70 and was significant higher than in control group (p=0.0011) and than in the WT tumors (p=0.0112). Consistent with this analysis, immunohistochemistry results showed a high expression of OLFM4 in the secretion vehicles in KRAS-mutated tissue as compared to non-mutated samples (FIG. 2D). This observation suggests that the glycosylated OLFM4 is probably secreted in these tumors.

The Ras/NF-κB2 Pathway Promotes OLFM4 Expression

In addition to OLFM4 glycosylation in KRAS-mutated tissues, we have noticed by immunohistostaining and western blot (FIGS. 2 & 3), an increase of OLFM4 expression. As a first step to analyze the effect of the ras oncogene on OLFM4 expression, we generated stable colorectal cell lines expressing the rasV12 oncogene under the control of a doxycycline-inducible promoter. Following a 48 hr induction, results showed an upregulation of the OLFM4 protein level (FIG. 4A). In addition, semi-quantitative PCR analysis showed that the Ras-mediated OLFM4 induction is regulated at the transcriptional level (FIG. 4B). Recent publications have shown that the NF-κB transcription factor regulates OLFM4 expression in myeloid and gastric cells. A transcription recognition site analysis of the OLFM4 promoter showed the presence of different potential NF-κB2 binding sites (FIG. 4C). To determine if NF-κB2 regulates OLFM4 expression in KRAS-mutated tumor, we analyzed its activation following rasV12 induction in our colorectal model. We observed that the NF-κB2 activation is correlated with the Ras-mediated OLFM4 expression in colorectal cell lines (FIG. 4A). Moreover, by using small interfering RNA assay, we noticed that a downregulation of NF-κB2 inhibits OLFM4 expression at the protein and RNA level (FIG. 4D-E). To determine if NF-κB2 regulates directly the OLFM4 promoter, chromatin immunoprecipitation assays (ChIP) have been performed in colorectal cell lines. These experiments showed a recruitment of NF-κB2 and its cofactor BCL3 on the initiation site of OLFM4 gene, which is correlated to the recruitment of the RNA polymerase II. These results suggest that Ras induces OLFM4 expression through NF-κB2 activation in colorectal cells.

The Secreted OLFM4 Promotes Resistance to SN38 and Oxaliplatin

To further explore the role of the OLFM4 in KRAS-mutated colorectal tumor, we have measured the survival rate of colorectal cells following genotoxic treatments in the presence or absence of OLFM4. As a first approach, we have generated HCT116 stable cell lines that contain an inducible vector expressing the OLFM4 cDNA. Clonogenic assays performed on these cells indicate that OLFM4 increased cell survival in response to oxaliplatin and sn38 as compared to wild type HCT116 cells (FIGS. 5A and C). Despite changes in oxaliplatin and sn38 sensitivity, the morphology (data not shown) and growth rate of the HCT116-OLFM4 and HCT116-WT were similar. To discriminate between the intra- and extra-cellular functions of OLFM4, HCT116 cells were treated with chemotherapeutic drugs in the presence or absence of OLFM4. By clonogenic assay, we have shown that the presence of OLFM4 in the media promotes resistance to the genotoxic agents, oxaliplatin and sn38, the active metabolite of irinotecan (FIGS. 5B and D). All differences were shown to be significant by statistical analysis. These results suggest that extracellular OLFM4 induces resistance to sn38 and oxaliplatin in colorectal cells.

REFERENCES

Boyle et al., in: *Management of Colorectal Cancer*. London, United Kingdom: Dunitz; 1998, p. 19-34.
Poston et al., *J Clin Oncol.*; 26: 4828-4833, 2008.
Bos, *Cancer Res.* 49, 4682-4689, 1989.
Jervoise et al., *J Natl Cancer Inst;* 90: 675-684, 1998
Andreyev et al., *Br J Cancer,* 85: 692-696, 2001
Etienne-Grimaldi et al., *Clin Cancer Res;* 14: 4830-4835, 2008
Roessler et al., *Clin Cancer Res.* 11: 6550-6657, 2005
Roessler et al., *Mol. Cell. Proteomics* 5: 2092-2101, 2006
Alfonso et al., *Proteomics,* 5: 2602-2611, 2005
Madoz-Gúrpide et al., *Mol. Cell. Proteomics* 6: 2150-2164, 2007

Uemura et al., *J. Biol. Chem.*, 283: 26428-26435, 2008
Bi et al., *Mol. Cell. Proteomics*, 5: 1119-1130, 2006
Li et al., *Mol. Cell. Proteomics*, 7: 1810-1823, 2008
14 Wang et al., *Mol. Cell. Proteomics*, 7: 1639-1650
Kranenburg O. *Biochem Biophys Acta;* 1756(2): 81-82, 2005.
Ernoult et al., *Proteome Sci.*, 136:27, 2008.
Zanivan et al., *Proteome Res;* 7(12): 5314-5326, 2008.
Schetter et al., *Clin Cancer Res*, 15(18): 5878-5887, 2009.
Zhang et al., *Gene;* 283: 83-93, 2002.
Koshida et al., *Cancer Sci;* 98: 315-20, 2007.
Liu et al., *Clin Cancer Res;* 14: 1041-1049, 2008
Zhang et al., *Cancer Res,* 64:2474-2481, 2004.
Kee et al. *Mol. Carcinogenesis,* 49: 259-270, 2010
Oue et al., *Int J Cancer,* 125(10): 2383-2392, 2009.
Tomarev & Nakaya, *Mol Neurobiol*, 40: 122-138, 2009.
Schwacke et al., *BMC Bioinformatics*, 10: 342. 2009
Grant et al., *J Proteome Res*, 8(9):4252-4263, 2009.

The invention claimed is:

1. A method of treating colorectal cancer, comprising:
   (a) determining the presence of a chemotherapeutic agent-responding or non-responding phenotype of a colorectal cancer patient, said determining comprising:
      (i) determining the expression level of OLFM4 in a biological sample of said patient, wherein said OLFM4 expression level is determined by:
         measuring the amount of the glycosylated form of the olfactomedin 4 protein;
         measuring the amount of the non glycosylated form of the olfactomedin 4 protein; and
         calculating the ration of glycosylated versus non glycosylated forms of the olfactomedin 4 protein;
      (ii) comparing the expression level with at least one reference expression level, and
      (iii) determining the chemotherapeutic agent responding or non-responding phenotype, wherein an expression level in step (i) higher than the reference expression level of step (iii) indicates a non-responding phenotype; and
   (b) administering to the patient a dose of chemotherapeutic agent, wherein said dose is higher than 0 and wherein the phenotype determined in step (a) is a responding phenotype.

2. The method of claim 1, wherein the chemotherapeutic agent is a genotoxic drug.

3. The method of claim 2, wherein the genotoxic drug is oxaliplatin or irinotecan.

4. The method of claim 1, wherein the chemotherapeutic agent is an EGFR-targeting agent.

5. The method of claim 4, wherein the EGFR-targeting agent is a monoclonal antibody.

6. The method of claim 5, wherein the monoclonal antibody is selected from the group consisting of panitumumab and cetuximab.

7. The method of claim 1, wherein said biological sample is selected from the group consisting of a serum sample, a plasma sample, an urine sample, a blood sample, a lymph sample, and a colorectal cancer sample.

8. The method of claim 1, wherein the biological sample is a blood sample.

9. The method of claim 1, wherein the biological sample is a colorectal cancer sample.

10. The method of claim 1, wherein said expression level is measured using specific antibodies or other membrane detection technologies.

11. The method of claim 1, wherein the ratio is greater than 1.4.

* * * * *